US00PP36324P2

(12) United States Plant Patent
Dirr et al.

(10) Patent No.: US PP36,324 P2
(45) Date of Patent: Dec. 17, 2024

(54) ***BUDDLEIA* PLANT NAMED 'BD-02-21'**

(50) Latin Name: *Buddleia davidii*
Varietal Denomination: BD-02-21

(71) Applicant: Premier Introductions, Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/373,340

(22) Filed: Sep. 27, 2023

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Buddleia* plant named 'BD-02-21', characterized by its compact, upright spreading habit, dark green foliage with silvery underside, numerous purple flowers, exceptionally free flowering (floriferous blooming habit), and long flowering season, with flowers produced from summer to the first frost. Persistence under heat and humidity.

3 Drawing Sheets

Genus and species of plant claimed: *Buddleia davidii.*
Variety denomination: 'BD-02-21'.

BACKGROUND OF THE INVENTION

The present invention relates to a new and distinct cultivar of *Buddleia* plant, botanically known as *Buddleia davidii,* commonly known as butterfly-bush, and hereinafter referred to by the cultivar name 'BD-02-21'. 'BD-02-21' is grown primarily as an ornamental for landscape use and for use as a potted plant.

'BD-02-21' originated from an open-pollination of the cultivar 'SMNBDO' (U.S. Plant Pat. No. 28,796) growing in Watkinsville, GA in 2021. The cultivar 'BD-02-21' originated and was selected in a cultivated environment in Watkinsville, GA from the progeny of this open-pollination by continued evaluation for growth habit, foliage, and flower characteristics.

Asexual reproduction of 'BD-02-21' by stem cuttings in Watkinsville, GA since 2021 has shown that all the unique features of this new *Buddleia,* as herein described, are stable and reproduced true-to-type through successive generations of such asexual propagation.

SUMMARY OF THE INVENTION

Plants of the new cultivar 'BD-02-21' have not been observed under all possible environmental conditions. The phenotype may vary somewhat with changes in light, temperature, soil, and rainfall without, however, any variance in genotype.

The following traits have been observed and represent the characteristics of the new cultivar. In combination these characteristics distinguish 'BD-02-21' from all other varieties in commerce known to the inventor.

1. Compact, upright spreading habit.

2. Dark green foliage with silvery underside.
3. Numerous purple flowers.
4. Exceptionally free flowering (floriferous blooming habit).
5. Long flowering season with flowers produced from spring to the first frost.
6. Persistence under nursery and garden culture.

PARENTAL COMPARISON

'BD-02-21' is distinguished from its female parent, 'SMNBDO', by its overall size, foliage color, flower color, and inflorescence size. 'BD-02-21' has an overall smaller size, dark green foliage, purple flower color and smaller inflorescences, whereas 'SMNBDO' has an overall larger size, yellow-green foliage, lilac-pink flower color and larger inflorescences.

'BD-02-21' can be compared to 'Botex 004' (U.S. Plant Pat. No. 34,378). 'BD-02-21' has purple inflorescences, dark-green foliage, and smaller overall size. 'Botex 004' has lilac-blue inflorescences, darker green foliage, and larger overall size.

BRIEF DESCRIPTION OF THE DRAWINGS

The accompanying color photographs illustrate the flower and foliage characteristics and the overall appearance of 'BD-02-21', showing the colors as true as it is reasonably possible to obtain in color reproductions of this type. Colors in the photographs may differ slightly from the color values cited in the detailed botanical description which accurately describe the colors of the new *Buddleia.*

DETAILED DESCRIPTION

Figure 1:
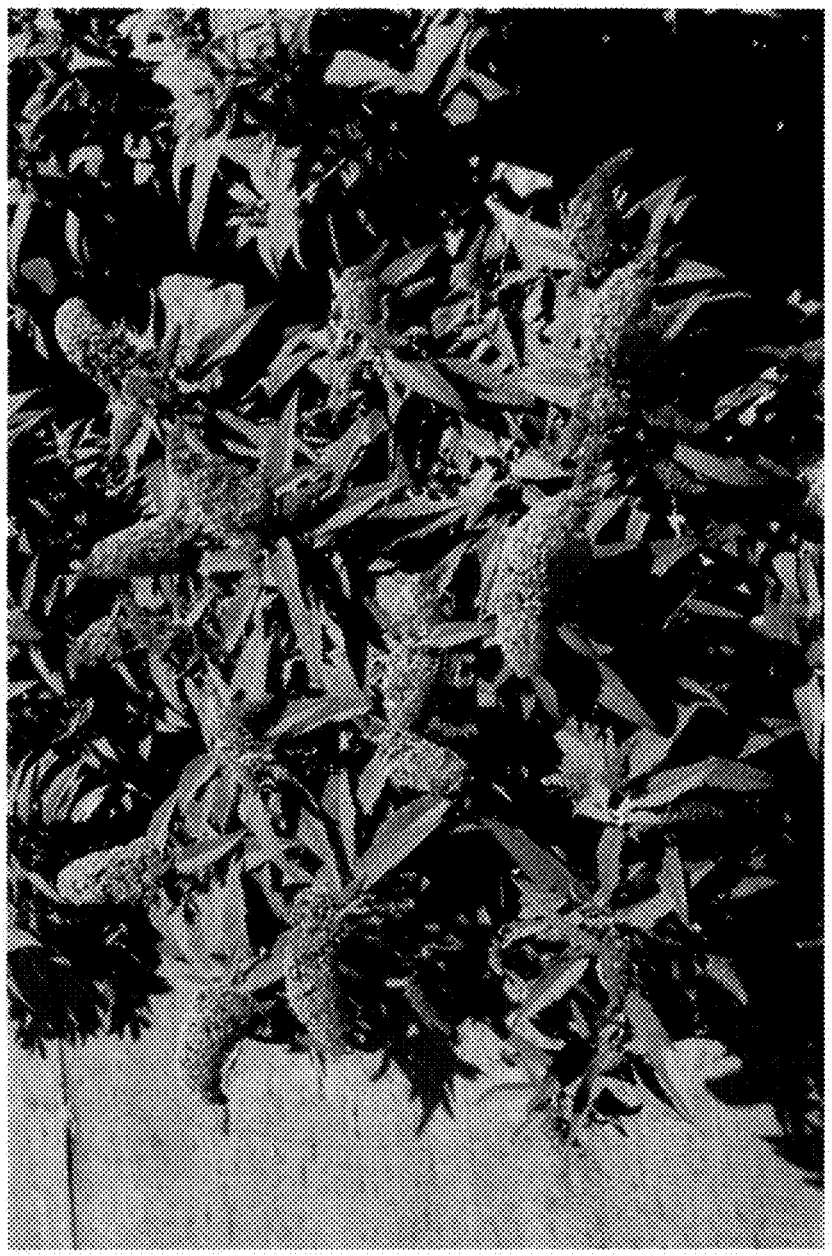
FIG. 1 Illustrates the overall appearance of a two-year-old container-grown plant of 'BD-02-21'.
Figure 2:
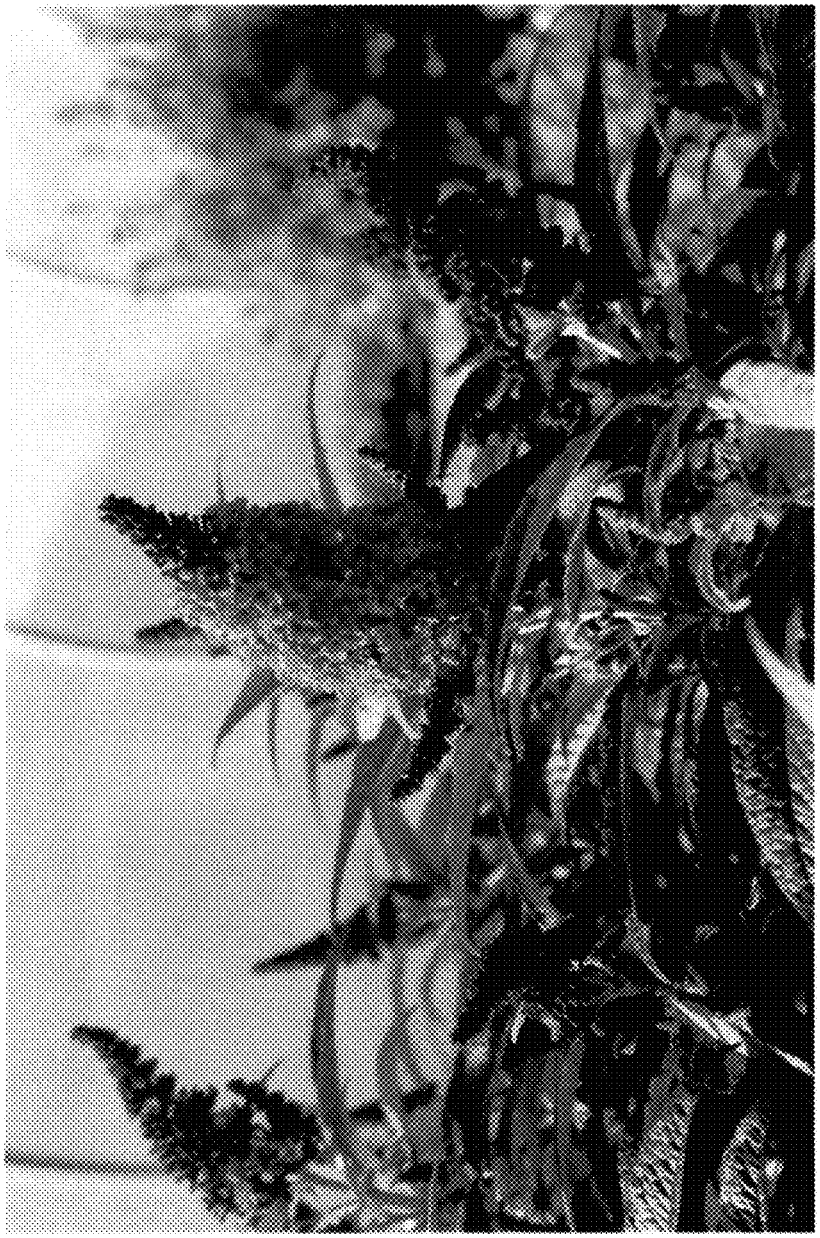
FIG. 2 Illustrates a close-up view of the inflorescences on a two-year-old plant of 'BD-02-21'.
Figure 3:
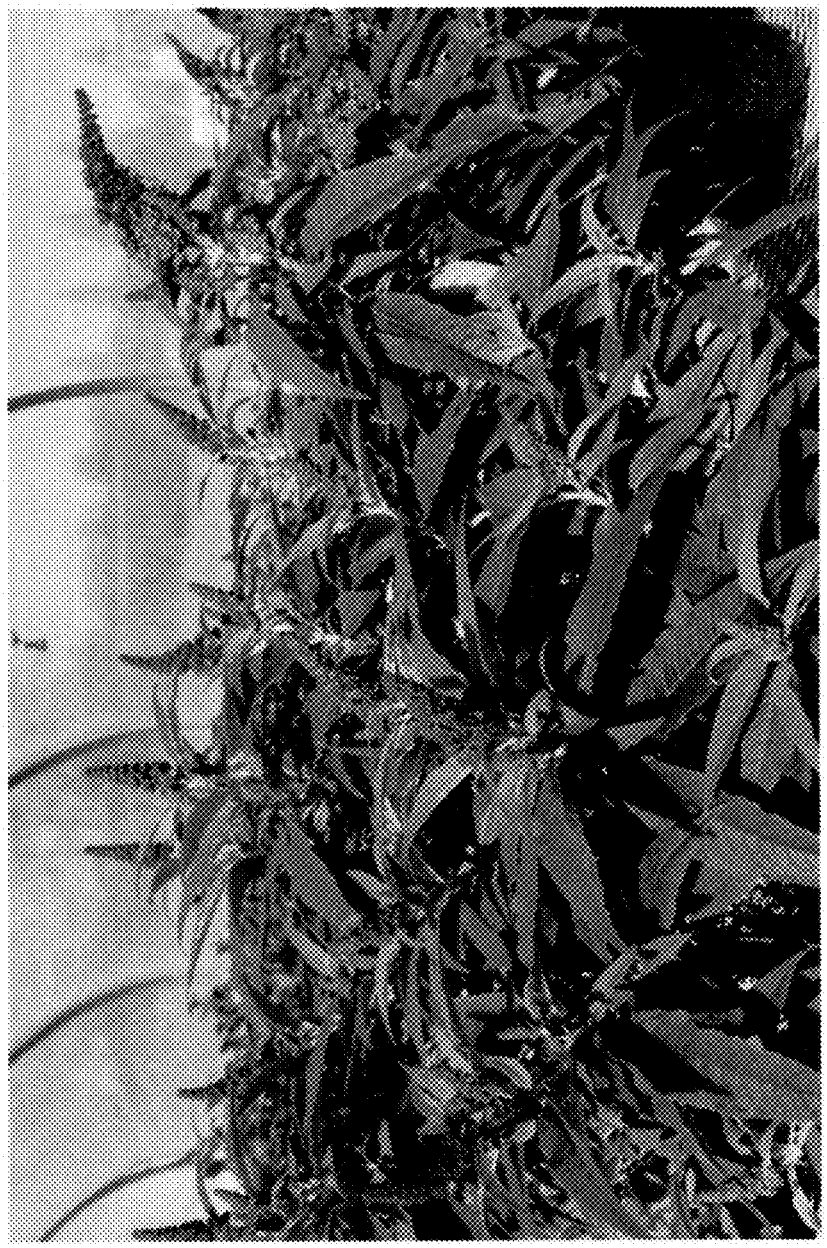
FIG. 3 Illustrates a view of several 3-gallon greenhouse-grown plants of 'BD-02-21'.

In the following description, color references are made to The Royal Horticultural Society Colour Chart, 2015 Edition, except where general terms of ordinary dictionary significance are used. Plants used for the description were approximately two years old and were grown in 11.36 L containers under outdoor conditions in Watkinsville, GA. Colors are described using The Royal Horticultural Society Colour Chart (R.H.S.).

Botanical classification: *Buddleia davidii* 'BD-02-21'.

Parentage: Female, or seed, parent: 'SMNBDO' (U.S. Plant Pat. No. 28,796).

Male, or pollen parent: Unknown (open-pollinated).

Propagation: Terminal cuttings.

Time to initiate roots, summer: About 21 days at 32° C.

Time to produce a finished plant, summer: About 12 weeks from softwood cuttings.

Plant description: Deciduous perennial shrub; compact, upright spreading plant, dense and bushy in appearance; short internodes, and thick stems.

*Root description*.—Numerous, fibrous, and well-branched. Color: 155A.

*Plant size*.—About 43 cm high from the soil level to the top of the inflorescences and about 56 cm wide.

*Lateral branches*.—Quantity: Freely branching habit with about 12 primary lateral branches developing per plant about 21 cm to 30 cm in length. Pinching enhances lateral branching. Erect about 35° from vertical.

*First year stems have a diameter of about* 4 *mm. Shape*.—Quadrangular when young, becoming square with age. Pubescence: tomentulose when young, becoming glabrous with age.

*Second year and older stems have a diameter of about* 5 *mm or more. Shape*.—Square.

*Trunk diameter*.—2.5 cm at the soil line. Color: 199A. Striations close to 156A.

*Internode length*.—About 4 cm.

*Strength*.—Flexible when young, becoming stronger with age.

*First year stem color* (*young*).—192C. Color (mature): 199B.

*Second year and older stem color*.—199A.

Vegetative buds: Opposite arrangement, naked, subglobose, 2 bud scales with tomentulose pubescence.

*Color*.—195B. Size: about 2 mm in length and 1 mm in width.

Foliage description:

*Quantity of leaves per branch*.—About 15-25. Arrangement: opposite, simple. Leaf length: about 8 cm. Leaf width: about 2.3 cm. Shape: lanceolate. Apex: acuminate. Base: cuneate. Margin: closely serrate to serrulate.

*Texture*.—Upper and lower surface slightly pubescent. Pubescence color on lower and upper surface near 145D.

*Venation pattern*.—Pinnate. Venation color (upper surface): NN137A. Venation color (lower surface): 149D.

*Foliage color* (*upper surface*).—NN137A. Foliage color (lower surface): 191D.

*Petiole length*.—About 5 mm. Petiole diameter: about 1 mm. Petiole color: 148D. Pubescence: tomentulose.

Flower description: Flowers on new growth. Flowers are produced from about June through the first frost in Watkinsville, GA. An inflorescence is showy for about two weeks, and individual flowers are salverform in shape and last about three days and are self-cleaning. Approximately 350-400 flowers per individual inflorescence. Flowers open from base to apex, acropetally.

*Inflorescence type*.—Terminal panicle. Inflorescence shape: conical-pyramidal. Inflorescence length: about 9-10 cm. Inflorescence width: about 3.5 cm. Fragrance: pleasant and sweet.

*Peduncle*.—About 0.5 cm in length, about 2 mm in diameter, strength-strong, color is N148D, with tomentulose pubescence.

*Individual flowers*.—About 8 mm-1 cm in height and 8 mm in diameter and salverform in shape.

*Flower buds*.—Length: about 4 mm; Diameter: about 1 mm; Color: N77B. Shape: lanceolate.

*Pedicels*.—About 1 mm in length, less than 1 mm in diameter, strength-moderately strong, 148D in color with tomentulose pubescence.

*Calyx*.—Consists of 4 sepals fused at the base. The calyx is about 3 mm in length, about 1 mm in diameter, 148D in color, tubular in shape with tomentulose pubescence. The individual sepals are lanceolate in shape, with an acute apex and entire margin, 148D in color with tomentulose pubescence.

Petals:

*Arrangement/appearance*.—4 petals fused at the base to form the corolla tube, which is about 1 cm in length, 1 mm in width, outer surface is 63B in color and the inner surface or center of the flower is N30A in color.

*Petal*.—Length: about 5 mm. Width: about 5 mm. Shape: broad spatulate. Apex: broad obtuse to rounded. Margin: ruffled. Texture: smooth and soft.

*Petal color*.—Upper surface and lower surface 76A in color.

*Corolla*.—Throat is about 9 mm in length, less than 1 mm in width, corolla tube color inside is N30A, corolla tube color outside is 63B, corolla tube surfaces pubescent, corolla tube shape is tubular, corolla lobe is semi-erect at full flowering and arrangement is free, present is an eye and it is N77A in color.

Stamens:

*Quantity/arrangement*.—4 stamens per flower, fused to the inner base of the corolla tube, about 2.5 mm long. Filaments: 1 mm in length, less than 0.5 mm in width, and N25B in color. Anthers: 1 mm in length, 0.5 mm in width, and NN155B in color. The stamens are not pubescent. Pollen: produced in small quantities and is 11C in color.

Pistils:

*Quantity*.—One superior pistil per flower. Pubescence: none. Pistil: about 1 mm in length and about 1 mm in width. Stigma: elongated shape, about 1 mm in length and 0.5 mm in width and 144B in color. Style: tubular in shape, about 1 mm in length, less than 0.5 mm in width and 144B in color. Ovary: ovoid in shape, about 2 mm in length, about 1 mm in width and 144B in color.

Fruit:

*Type/appearance*.—Two-valved, septicidal dehiscent capsule. Length: about 7 mm. Width: about 2 mm. Immature color: 143A. Mature color: N200D. Each capsule contains several tiny seeds 164D in color.

Disease/pest resistance: 'BD-02-21' has not exhibited any particular pest or disease susceptibility or resistance, except occasional susceptibility to spider mites (*Tetranychus urticae*) under very hot and dry conditions. 'BD-02-21' is cold hardy to USDA Hardiness Zones 5-9.

We claim:

1. A new and distinct *Buddleia* plant named 'BD-02-21', as illustrated and described herein.

* * * * *